(12) United States Patent
Tallberg

(10) Patent No.: US 8,110,227 B2
(45) Date of Patent: Feb. 7, 2012

(54) DAIRY BASED FOODSTUFF CONTAINING CENTRAL NERVOUS SYSTEM LIPIDS

(75) Inventor: Thomas Tallberg, Helsinki (FI)

(73) Assignee: Oy Neurofood AB, Espoo (FI)

( * ) Notice: Subject to any disclaimer, the term of this patent is extended or adjusted under 35 U.S.C. 154(b) by 345 days.

(21) Appl. No.: 12/304,780

(22) PCT Filed: Jun. 13, 2007

(86) PCT No.: PCT/FI2007/050353
§ 371 (c)(1),
(2), (4) Date: Dec. 15, 2008

(87) PCT Pub. No.: WO2007/144472
PCT Pub. Date: Dec. 21, 2007

(65) Prior Publication Data
US 2009/0208587 A1    Aug. 20, 2009

(30) Foreign Application Priority Data
Jun. 16, 2006  (FI) ...................................... 20065414

(51) Int. Cl.
*A61K 35/30* (2006.01)
(52) U.S. Cl. ........................................ 424/570; 424/439
(58) Field of Classification Search .................. None
See application file for complete search history.

(56) References Cited

U.S. PATENT DOCUMENTS

| | | | |
|---|---|---|---|
| 5,591,479 A | 1/1997 | Ponroy | |
| 5,684,133 A | 11/1997 | Schwab et al. | |
| 5,709,888 A * | 1/1998 | Gil et al. | 424/522 |
| 5,853,747 A | 12/1998 | Ponroy | |
| 7,687,094 B2 * | 3/2010 | Ladd et al. | 426/548 |
| 2007/0032548 A1 * | 2/2007 | Ellis | 514/547 |

FOREIGN PATENT DOCUMENTS

| | | |
|---|---|---|
| EP | 0 484 266 | 5/1992 |
| EP | 0 661 056 | 7/1995 |
| EP | 0 815 735 A2 | 1/1998 |
| GB | 1 507 754 | 4/1978 |
| JP | 11-35587 | 2/1999 |
| WO | 92/22291 | 12/1992 |
| WO | 02/34062 | 5/2002 |

OTHER PUBLICATIONS

Entenman, C., Lectures of the 1961 Short Course on Newer Lipid Analyses, Part I, The Preparation of Tissue Lipid Extracts, p. 534-538.*
Jouppila et al., J Dairy Science, 1994, vol. 77, p. 2907-2915.*
Patent Abstracts of Japan of JP 11-35587 dated Feb. 9, 1999.
Vesper, H., et al. "Sphingolipids in Food and the Emerging Importance of Sphingolipids to Nutrition." Journal of Nutrition, Wistar Institute of Anatomy and Biology (Jul. 1999) vol. 129, No. 7, pp. 1239-1250.
Ahn, Eun-Hyun, et al. "Bioactive Sphingolipids are Significant Constituents of Foods." FASEB Journal, Fed. of American Soc. For Experimental Biology (1998) vol. 12, No. 4, pp. A210.
Bourrre, J. M. "Omega-3 fatty acids in psychiatry Acides gras omega-3 et troubles psychiatriques." M/S Medecine Sciences, Societe Des Periodiques Flammarion (Feb. 2005) vol. 21, No. 2 pp. 216-221.
Office Action from the Russian Patent Office dated Sep. 10, 2010 in respect of corresponding Russian Patent Application No. 2008152249.

* cited by examiner

*Primary Examiner* — Kade Ariani
(74) *Attorney, Agent, or Firm* — Ladas & Parry LLP

(57) ABSTRACT

The central nervous system (CNS), i.e. the spinal cord and the brain, contains a large amount of various lipids, collectively called CNS lipids. These lipids are essential for embryonic induction but are also active in the adult body in keeping our cells in healthy normal function. By actively incorporating these normal vital CNS lipids in functional foodstuffs, it is possible to improve the immunity of a person by ingestion of such foodstuffs. The problem associated with the addition of brain substance to the diet is associated with bad taste and unpleasant attributes of the brain substance. The present invention discloses CNS lipids containing foodstuffs without the unpleasant taste and other attributes of the brain substance. The present invention relates to dairy based foodstuffs where normal fats and lipids have been replaced by CNS lipids.

6 Claims, No Drawings

DAIRY BASED FOODSTUFF CONTAINING CENTRAL NERVOUS SYSTEM LIPIDS

FIELD OF INVENTION

The present invention generally relates to foodstuff with health sustaining and improving functions. Specifically, the present invention relates to dairy based foodstuff containing vital lipids originating from the central nervous system, especially from prion-free piglet brain, spinal cord and brain membranes.

BACKGROUND OF THE INVENTION

The central nervous system (CNS), i.e. the spinal cord and the brain, contains a large amount of various lipids, collectively called CNS lipids. These lipids are not only essential for embryonic induction but also active in the adult body in keeping our cells in normal healthy function. This central regulatory function, lipidomics, co-operates with genomics and proteomics to secure normal gene-transcription and to support our health. The lipids are also essential for normal embryogenesis and fetal development.

Deficiency of CNS lipids may cause various aberrations in the form of disparate neurogenic ailments, such as stress, anxiety, pain, sleep disorder, stiffness, atherosclerosis, disturbances in blood circulation etc. These special forms of neurogenic dysfunctions, "Tallbergs syndromes" [1], are schematically described in Table 1. These symptoms may be curtailed in a person, without side-effects, following administration of the CNS lipids together with a normal diet. CNS lipids may be absorbed from the intestine and be incorporated in our nervous system securing healthy synaptogenesis and bodily functions. The nervous system of patients, endogenously lacking or having a deficient production of CNS lipids, seems to be able to up-take these vital lipids from a diet containing CNS lipids.

By actively incorporating these normal vital CNS lipids in functional foodstuff, it is possible to improve the immunity of a person by ingesting such foodstuffs. CNS lipids also contain a lymphopoietic vitamin substance. CNS lipids alleviate diverse neurogenic ailments, such as burn-out syndromes, sleep disorders, hyperesthesia, muscular stiffness, chronic inflammatory reactions, and measurably restore the normal health condition in a person.

TABLE 1

Lipidomics; Patients healthy organ induction and cancer control is linked to a balanced internal milieu in their millions of CNS lipid molecules Embryogenesis
  Intellect, fantasy, memory
  Inductional CNS is linked to our cancer control
  Blood-brain barrier lesions upset this control (herpes)
  CNS lipid ingestion may alleviate pain
  Melanoma satellites, appear in the enervated axonal area
  Lymphopoiesis is stimulated by CNS lipids, linked to Ti [=Co in $B_{12}$]
  Cholesterol dip after CNS lipid and blood-barrier membrane ingestion
  Regional CNS lipid depletion in the spinal cord a link to atherosclerosis?
  Burn-out syndromes and stress are alleviated by a prion-free CNS diet
  Lipid CNS monomers may be involved in controlling allergic reactions
  Idiopathic pains "Tallberg syndromes" are mitigated by dietary CNS lipids
  CNS lipid signals match the cellular membrane receptor lipid structures
  Increased incidence of Autism and ADHD may be caused by deficient intake of natural lipids uring pregnancy, a sequel of the cholesterol fad?
  Mitochondrial regulation of the genome is in concert with lipidomics, enomics and proteomics.

CNS lipids are easily incorporated in the daily diet in the form of brain substance added to the normal diet. The problem associated with the addition of brain substance to the diet is the bad taste and unpleasant attributes associated with the brain substance. The present invention discloses a foodstuff containing CNS lipids without the unpleasant taste and attributes associated with the use of brain substance.

SUMMARY OF THE INVENTION

This invention is related to dairy based foodstuff containing central nervous system lipids (CNS lipids). The source for the CNS lipids is either whole brain substance or specific lipid molecules extracted from the whole brain substance.

This invention further relates to the use of a dairy based foodstuff according to the present invention as dietary supplements in the prophylaxis and treatment of ailments, such as certain forms of cancer, generated by deficiency of vital central nervous system lipids.

DETAILED DESCRIPTION OF THE INVENTION

The present invention describes a dairy based foodstuff containing central nervous system lipids (CNS lipids). In the manufacture of the dairy based foodstuffs substantially all of the fat and lipids originate from brain substance, spinal cord and brain membranes. Foodstuffs according to the present invention are completely free of the unpleasant taste and other negative attributes associated with brain substance. The foodstuffs are tasteful and can be manufactured into products that have a high appeal to consumers. It is essential that what is called as functional food not only has health sustaining and improving properties but also appeals to the consumer.

The term "a dairy based foodstuff" should be interpreted to refer to conventional dairy products and also foodstuff based on milk-type substances such as coconut milk and soya milk. Dairy based foodstuff is understood to include various frozen products such as ice-cream, frozen yoghurt, frozen milkshakes, but also non-frozen products such as yoghurt, milkshakes, custards, curd cheese and sour milk products etc.

In the manufacture of the foodstuff according to the present invention CNS lipids replace substantially all other lipids normally present in dairy products. The replacing CNS lipids can be in the form of prion-free whole brain substance including brain membranes and spinal cord lipids. The brain is isolated and cooked and then dried. The remaining substance can be directly mixed with e.g. milk and fruits and be used as a basic ingredient in the manufacture of the dairy based foodstuffs. If the whole brain is used as the source of CNS lipids the CNS lipid containing substance also contains other vital compounds present in the brain such as a lymphopoietic vitamin substance. Prion-free piglet brain can preferably be used as the source of the whole brain substance. The spinal chord and the brain membranes of the piglet can also be used as a source for CNS lipids.

The CNS lipids can also be extracted from the whole brain substance. In this embodiment of the invention the cooked brain is freeze-dried. The total lipid content is extracted from the freeze-dried brain substance with a suitable organic solvents e.g. ether/alcohol. The organic phase, containing the CNS lipids, may be filtered prior to evaporating (distilling) the organic solvent. The remains can be further purified or used as such in food formulation.

It is very essential that the source of the CNS lipid is absolutely free from prions, i.e. either piglet brain or extract of lyophilized brain etc. Prions are infectious agents composed only of proteins. Prions have been associated with diseases such as BSE (mad cow disease) and Creutzfeld-Jakob disease in humans. Since prions are proteins they will not be extracted with organic solvents from the brain substance together with the lipids. Lipid extracts of brain substance is therefore completely free from prions.

The CNS lipids in form of whole brain (including membranes and spinal cord) or extracted lipids, are used in the manufacture of the dairy based foodstuff. CNS lipids may replace all other forms of fat or lipid normally present in dairy products. CNS lipids mixed with assorted fruits, for the sake of taste, are used as the basic ingredient in food formulation.

Dairy based foodstuffs according to the present invention can also contain other taste enhancing ingredients. Examples of taste enhancing ingredients are e.g. natural and synthetic aromas, sweeteners, sugars, fruits and berries etc. Also other components, such as emulsifiers and thickeners, may be present in the foodstuff.

Foodstuff containing CNS lipids are useful as dietary supplements in the treatment and prophylaxis of various ailments and disorders that are generated due to deficiency of naturally occurring CNS lipids. Examples of such ailments are certain forms of cancer, e.g. basalioma and other disorders are (but not limited to): stress, anxiety, pain, sleep disorders, stiffness, atherosclerosis, Autism, ADHD, battle fatigue, posttraumatic stress syndrome disease, fibromyalgia and disturbances in blood circulation.

The CNS lipids enforced with other natural essential components may be used to compensate for genetic weaknesses. A physiologic supplementation of the causative metabolic dysfunction can be compensated but usually not corrected.

The CNS lipids can be made into special functional food items aimed to correct the metabolic deficiency which leads to certain forms of cancer. In that case the additive ingredients are then consist of certain aminoacids and essential trace-element salts.

EXAMPLES

Example 1

Use of Whole Brain as a Source of CNS Lipids

The whole brain and spinal cord from piglets is removed and washed. The brain substance is cooked for 30 minutes. The prion-free brain substance is used directly in the formulation of foodstuff. The cooked brain is mixed with fruits and this mixture acts as the starting material and basic ingredient in the manufacture of the dairy product, e.g. as ice-cream.

Example 2

Extraction of CNS Lipids from Brain

The piglet brain is lyophilized as in Example 1, and the cooked brain is extracted with ether/ethanol (70/30 vol-%) for three days. The CNS lipids dissolve in the organic solvent and the remains are removed by filtration. The organic solvent is evaporated (distilled) to dryness and the remains are used as a CNS lipid source in the manufacture of dairy products.

Example 3

Manufacturing Dairy Based Products

A. The CNS lipids are processed in a food mixer with the addition of orange, banana, lemon, lime, coconut milk, but no sugar is added. The mixture is thoroughly homogenized in a food-blender and then frozen to form ice-cream, or alternatively ingested as a "milk-shake".

B. The CNS lipids in a lyophilized forms are added to milk and may be used as a basic ingredient in various soups, bakeries, meat balls etc.

REFERENCES

[1] *Journal of the Australasian College of Nutritional and Environmental Medicine* (2005) vol 24, No 3, pp 3-9.

The invention claimed is:

1. A dairy based foodstuff, containing 50-100% (w/w) cooked prion-free whole brain substance as the total fat content wherein the dairy-based foodstuff is in frozen form.

2. The dairy based foodstuff according to claim 1, wherein the cooked prion-free whole brain substance is piglet brain substance.

3. The dairy based foodstuff according to claim 1, wherein said dairy based foodstuff is ice-cream.

4. The dairy based foodstuff according to claim 1, wherein said dairy based foodstuff also contains taste enhancing ingredients.

5. A method of prophylaxis and treatment of ailments and disorders generated by a deficiency of vital central nervous system lipids wherein the method comprises administration of a dairy based foodstuff according to claim 1, to an individual in need thereof.

6. The dairy based foodstuff according to claim 4, wherein said taste enhancing ingredients are selected from the group consisting of natural and synthetic aromas, sweeteners, sugars, fruits, berries, other components and mixtures thereof.

* * * * *